US00PP36046P2

(12) United States Plant Patent
Sanabria Aguilar et al.

(10) Patent No.: US PP36,046 P2
(45) Date of Patent: Jul. 30, 2024

(54) BLUEBERRY PLANT VARIETY NAMED 'BLUECSOL3'

(50) Latin Name: ***Vaccinium corymbosum* L.**
Varietal Denomination: BLUECSOL3

(71) Applicant: CAMPOSOL S.A., Lima (PE)

(72) Inventors: Kimberlayn Maria Apsara Sanabria Aguilar, Lima (PE); Milagros Janet Granda Mogollon De Montoya, Lima (PE); Luis Jose Montgomery Taboada, Lima (PE); Jorge David Romero Pajares, Lima (PE)

(73) Assignee: Camposol S.A., Lima (PE)

( * ) Notice: Subject to any disclaimer, the term of this patent is extended or adjusted under 35 U.S.C. 154(b) by 0 days.

(21) Appl. No.: 18/445,355

(22) Filed: Jul. 27, 2023

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Ladas & Parry LLP

(57) ABSTRACT

A new and distinct evergreen blueberry variety with zero chill requirement named 'BLUECSOL3', characterized by the following combination of traits: medium plant vigor, upright growth habit, ovate leaf shape, globose corolla shape and oblate fruit shaped, extra-large fruit size, very strong bloom intensity, medium sweetness and acidity, and firm fruit. Latin name of the genus and species: *Vaccinium corymbosum* L.

6 Drawing Sheets

Latin name: *Vaccinium corymbosum* L.
Variety denomination: Blueberry plant named 'BLUECSOL3'.

BACKGROUND OF THE INVENTION

The present invention relates to a new *Vaccinium corymbosum* L. plant, which was selected from open pollination between 'Biloxi' (*Vaccinium corymbosum* L., Unpatented) as the female (seed) parent and pollen from an unknown variety. Berry seeds of plants of 'Biloxi' were collected from different fields, located in Viru, La Libertad, Peru at the beginnings of 2016. 11805 seedlings at high density were planted under field conditions in December of the same year.

The seedlings were evaluated during 3 growing season (2017, 2018 and 2019) and the breeding method used was phenotypic recurrent selection. In December 2019 one of the seedlings, 'BLUECSOL3', was isolated due to its excellent quality fruit, long postharvest life, and high yield potential. 'BLUECSOL3' was asexually propagated by softwood cuttings to confirm the distinctness, and stability of the characteristics observed in another growing season. 5 rooted cuttings were planted in an experimental test plot, located in Viru, La Libertad, Peru. From December 2020 until the present, said test plot has shown that the unique features of this new *Vaccinium* variety are stable and reproduce true to type in successive generations of asexual propagation. In addition, 'BLUECSOL3' was subsequently propagated by softwood cutting and tissue culture and an additional plot, with 530 plants were planted in December 2021 in the same location. At the end of the growing season, 'BLUECSOL3' presented distinctness and stability of the agronomic characteristics for which it was selected.

SUMMARY OF THE VARIETY

The following are the most distinguishing traits of this new variety 'BLUECSOL3': medium plant vigor, upright growth habit, ovate leaf shape, globose corolla shape and oblate fruit shaped, extra-large fruit size, very strong bloom intensity, medium sweetness and acidity, and firm fruit.

'BLUECSOL3' was selected as an early variety, with high yield potential, excellent fruit quality and post-harvest life.

BRIEF DESCRIPTION OF THE DRAWINGS

The accompanying photographs show typical bush, leaves, flower, and fruit characteristics of the new *Vaccinium corymbosum* L. 'BLUECSOL3'. Colors shown are as accurate as can be reasonably reproduced by the photographic means. Photographs were taken of 2 and 5-year-old plants grown in fields located in Viru, La Libertad, Peru.

DETAILED BOTANICAL DESCRIPTION

Figure 1:
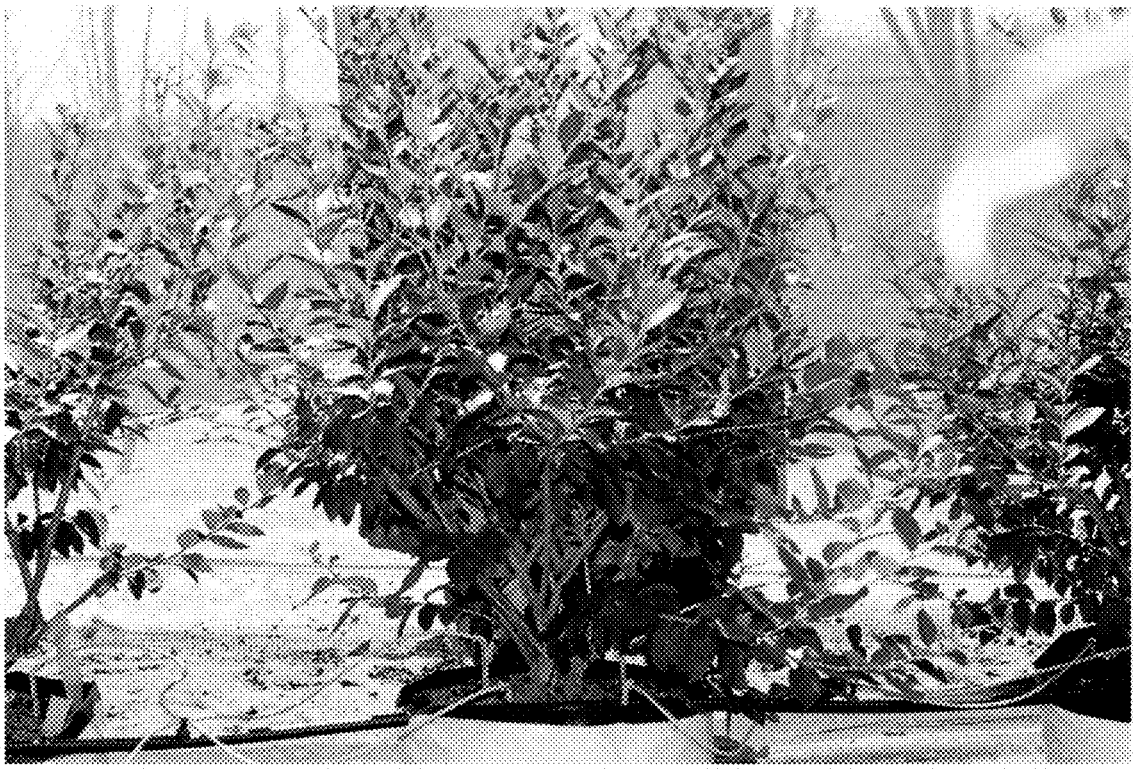
FIG. 1.—Shows typical bush with upright growth habit on 2-year-old plant of the new variety 'BLUECSOL3'.
Figure 2:
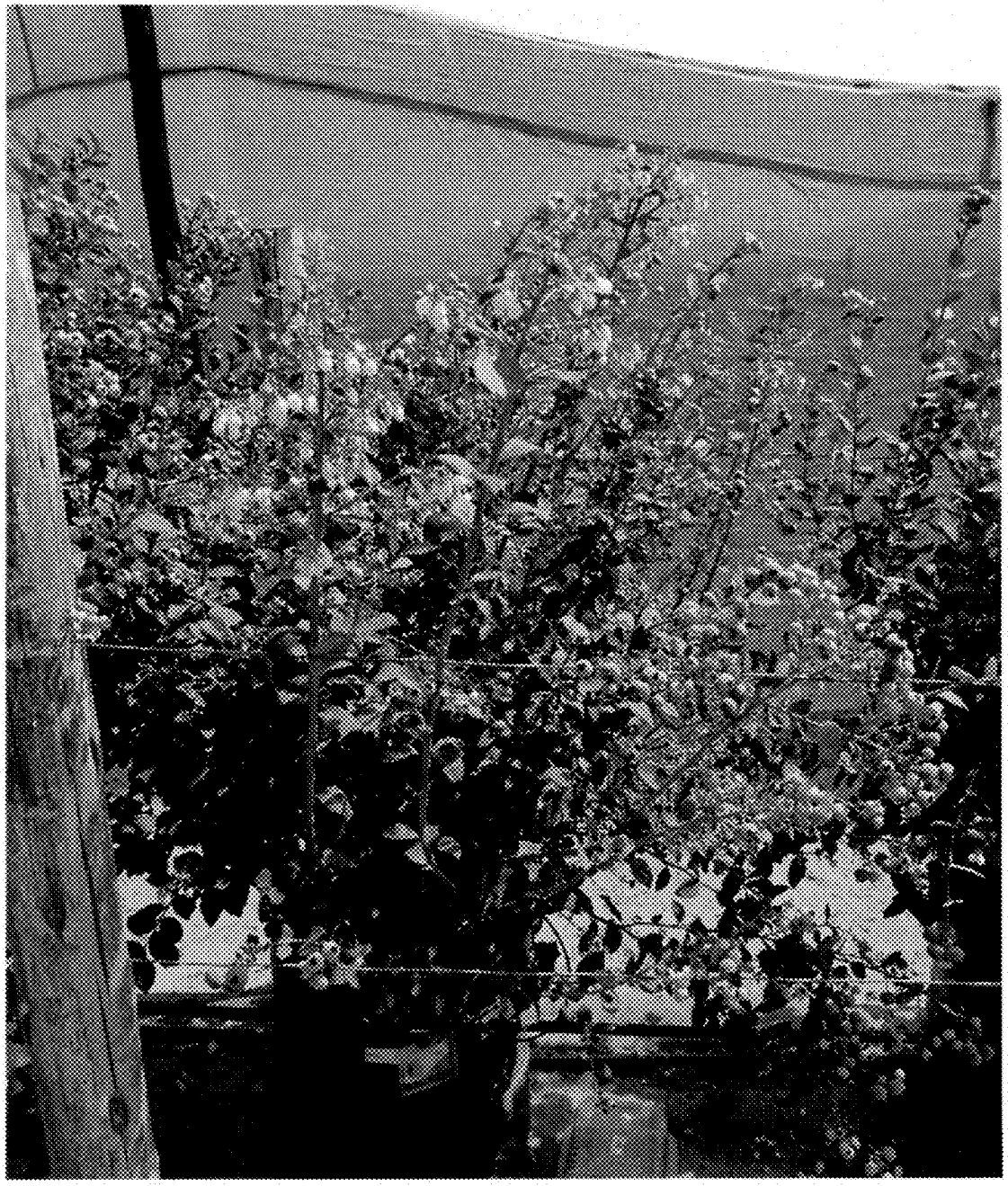
FIG. 2.—Shows typical bush with upright growth habit on 5-year-old plant of the new variety 'BLUECSOL3'.
Figure 3:
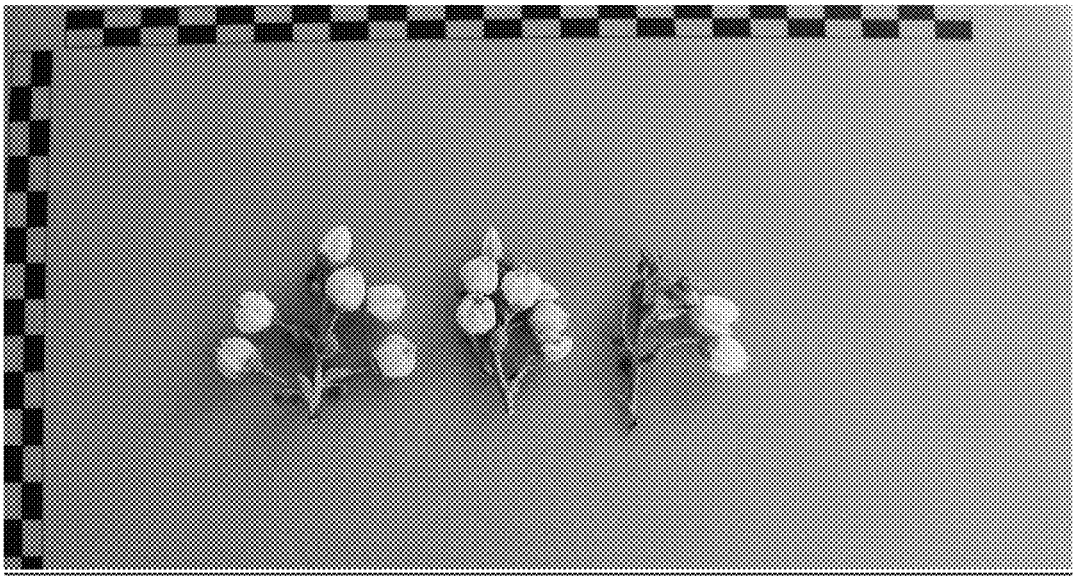
FIG. 3.—Shows the inflorescence length on 2-year-old plant of the new variety 'BLUECSOL3'.
Figure 4:
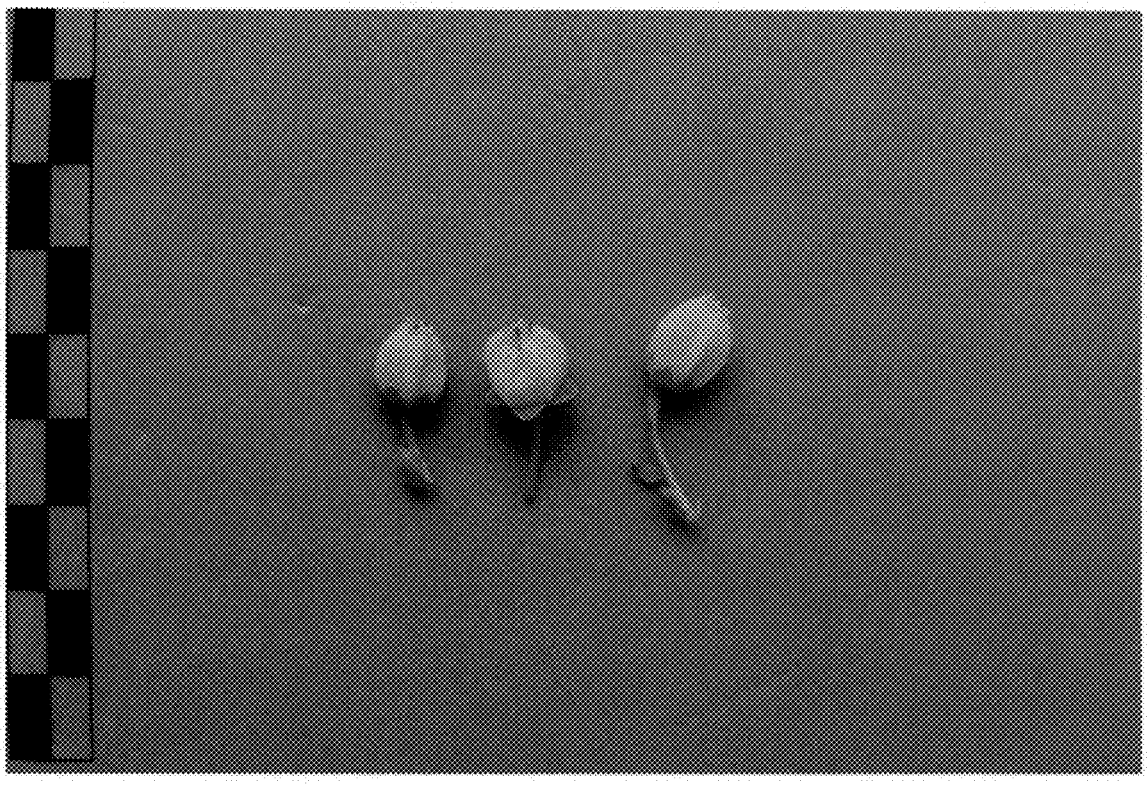
FIG. 4.—Shows the size and shape of the flower corolla on 2-year-old plant of the new variety 'BLUECSOL3'.
Figure 5:
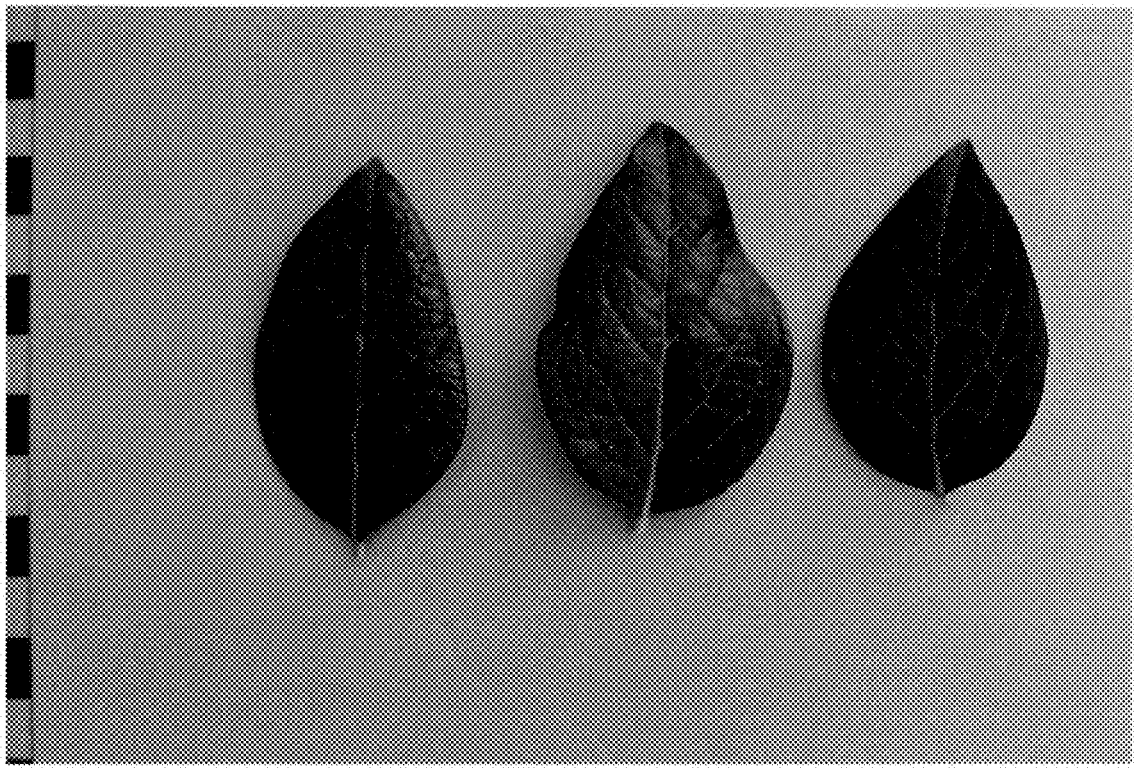
FIG. 5.—Shows the upper sides and shape of complete leaves on 2-year-old plant of the new variety 'BLUECSOL3'.
Figure 6:
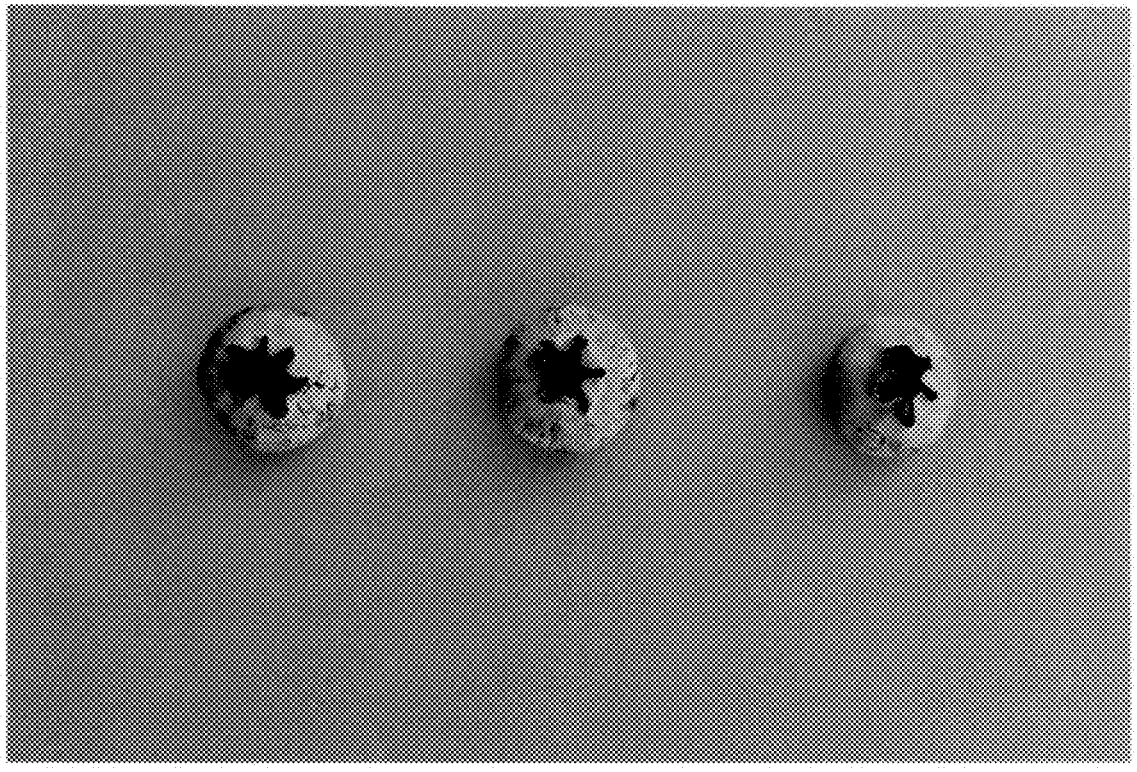
FIG. 6.—Shows the size and shape of the fruits on 2-year-old plant of the new variety 'BLUECSOL3'.

The following botanical description detailed forth distinctive traits of 'BLUECSOL3'. The data were collected from clones stablished in an experimental test plot in Peru on 2-year-old plants. Color descriptions are based on the Munsell® Plant Tissue Color Book scale of 2012 and Pantone® color codes of 2023.

Classification:

*Family.*—Ericaceae.

*Species.*—*Vaccinium corymbosum L.*

*Common name.*—Southem Highbush Blueberry.

*Variety name.*—'BLUECSOL3'.

Parentage:

*Female parent.*—'Biloxi' (Unpatented).

*Male parent.*—Unidentified variety.

Plant:

*Vigor.*—Medium.

*Growth habit.*—Upright.

*Height.*—Mean of 64 cm.

*Width.*—Mean of 81 cm.

*Internode length.*—Mean of 19.5 mm.

*Evergreenness.*—Evergreen.

*Chilling requirements.*—0 hours below 7° C.

*Color of 1-year-old rough bark observed Jun 23.*—Green Pantone® 5GY 6/6.

*Color of 1-year-old shoot observed Jun 23.*—Green Munsell® 2.5GY 6/4.

*Time of beginning vegetative growth.*—Early.

Propagation:

*Ease of propagation.*—Propagates readily from softwood cuttings and tissue culture.

*Type.*—By Tissue culture.

*Root description.*—'BLUECSOL3' develops deep root systems and moderate volume of roots in the topsoil layer.

*Rooting habit.*—Moderate density and branching.

Leaves:

*Length.*—Mean of 67 mm.

*Width.*—Mean of 36 mm.

*Length/width ratio.*—1.86.

*Shape.*—Ovate.

*Margin.*—Serrate.

*Color on upper side of old leaves.*—Green Munsell® 5GY 3/4.

*Color on upper side of young leaves.*—Green Munsell® 5GY 4/4.

Flowers:

*Flower cluster.*—Short.

*Flower fragrance.*—Faint smell of geranium flowers.

*Inflorescence length.*—Mean of 2.3 cm.

*Size of corolla tube.*—Mean of 11.6 mm (from pedicel attachment point to corolla tip excluding the pedicel).

*Corolla shape.*—Globose.

*Style length.*—Top of ovary to stigma tip. 10 mm.

*Time of beginning flowering on a one-year-old shoot.*—Early.

*Time of beginning of flowering on the current season's shoot.*—Early.

Fruits:

*Diameter of calyx aperture on mature berry.*—Mean of 6.2 mm.

*Depth of calyx on mature berry.*—Mean of 2.8 mm.

*Detachment force for ripe berries* (*easy, medium, hard*).—Easy.

*Berries per cluster.*—About 7 to 13.

*Density of the infructescence.*—Medium.

*Width.*—About 19 to 22 mm.

*Weight.*—Mean of 2.9 g per berry.

*Shape.*—Oblate.

*Intensity of fruit bloom.*—Very strong.

*Pedicel scar.*—Mean of 3.7 mm.

*Color of unripe fruit.*—Light green Munsell® 2.5GY 6/10.

*Color of mature fruit skin with bloom.*—Dapple gray Pantone® 16-3907 TCX.

*Color of mature fruit skin without bloom.*—Dark navy Pantone® 19-4013 TCX.

*Fruit firmness.*—Firm.

*Fruit acidity.*—Medium.

*Fruit sweetness.*—Medium.

*Fruiting type of the plant.*—One-year-old shoots and currents season shoots.

*Time of beginning of fruit ripening on one-year-old shoot.*—Early.

*Time of beginning of fruit ripening on the current season's shoot.*—Early.

*Market use of fruit.*—Fresh market.

Seeds:

*Color.*—Brown Munsell® 5YR 4/6.

*Seeds per berry.*—Mean of 8 seeds.

Reproductive organs:

*Pollen abundance.*—Low.

*Powdery mildew.* (*Erysiphe elevate*).—Slight susceptible.

*Insects, and mites.*—No sensitivity to any pest has been observed for 'BLUECSOL3'.

COMPARISON TO THE PARENTS

'BLUECSOL3' is distinguished of 'Biloxi' variety in the following characteristics:

Growth habit in 'Biloxi' (Unpatented) is semi-upright and in 'BLUECSOL3' is upright.

Length of internode in one-year-old shoot in 'Biloxi' (Unpatented) is medium and in 'BLUECSOL3' is long.

Anthocyanin coloration in the flower bud is weak in 'Biloxi' (Unpatented), whereas in 'BLUECSOL3' is medium.

Inflorescence length in 'Biloxi' (Unpatented) is medium, whereas in 'BLUECSOL3' is short.

Fruit size of 'Biloxi (Unpatented) is medium, whereas in 'BLUECSOL3' fruit size extra-large fruits.

Fruit firmness in 'BLUECSOL3' is greater than the fruit firmness in 'Biloxi (Unpatented).

Intensity of fruit bloom in 'Biloxi' (Unpatented) is medium and in 'BLUECSOL3' is strong.

COMPARISON TO COMMERCIAL VARIETY

'BLUECSOL3' differs from the commercial variety 'Emerald' (U.S. Plant Pat. No. 12,165) in the following characteristics:

Length of internode in one-year-old shoot in 'Emerald' (U.S. Plant Pat. No. 12,165) is short and in 'BLUECSOL3' is long.

The margin of the leaf in 'Emerald' (U.S. Plant Pat. No. 12,165) is entire and in 'BLUECSOL3' is serrate.

Shape of corolla is cylindric in 'Emerald' (U.S. Plant Pat. No. 12,165), whereas in 'BLUECSOL3' is globose.

Fruit size of 'Emerald' (U.S. Plant Pat. No. 12,165) is medium, whereas in 'BLUECSOL3' fruit size extra-large fruits.

Fruit firmness in 'BLUECSOL3' is greater than the fruit firmness in 'Emerald' (U.S. Plant Pat. No. 12,165).

Diameter of calyx basin in 'Emerald' (U.S. Plant Pat. No. 12,165) is medium, whereas the diameter of calyx basin in 'BLUECSOL3' is small.

Intensity of fruit bloom in 'Emerald' (U.S. Plant Pat. No. 12,165) is medium and in 'BLUECSOL3' is strong.

What is claimed is:

1. A new and distinct blueberry plant named 'BLUECSOL3' substantially as illustrated and described.

* * * * *